United States Patent [19]

Levine

[11] Patent Number: 4,727,878

[45] Date of Patent: Mar. 1, 1988

[54] FUNCTIONAL ELECTRICAL STIMULATION FOR PRESSURE SORE INHIBITION

[75] Inventor: Simon P. Levine, Ann Arbor, Mich.

[73] Assignee: The University of Michigan, Ann Arbor, Mich.

[21] Appl. No.: 780,565

[22] Filed: Sep. 26, 1985

[51] Int. Cl.$^4$ .............................................. A61N 1/32
[52] U.S. Cl. ............................... 128/419 R; 128/1 R; 128/421
[58] Field of Search ..... 128/419 R, 419 PG, 420–423, 128/1 R

[56] References Cited

U.S. PATENT DOCUMENTS

| | | | |
|---|---|---|---|
| 3,279,468 | 10/1966 | LeVine | 128/419 R |
| 4,019,510 | 4/1977 | Ellis | 128/421 |
| 4,180,078 | 12/1979 | Anderson | 128/419 PG |
| 4,342,317 | 8/1982 | Axelgaard | 128/421 |
| 4,554,923 | 11/1985 | Batters | 128/421 |

FOREIGN PATENT DOCUMENTS

| | | | |
|---|---|---|---|
| 2500415 | 7/1976 | Fed. Rep. of Germany | 128/421 |
| 2296437 | 9/1976 | France | 128/421 |
| 2504395 | 10/1982 | France | 128/421 |
| 625717 | 9/1978 | U.S.S.R. | 128/421 |
| 1044291 | 9/1983 | U.S.S.R. | 128/421 |

OTHER PUBLICATIONS

"The Medtronic Respond TM Neuromuscular Stimulator", 3/28/83.

Primary Examiner—William E. Kamm
Assistant Examiner—David Shay
Attorney, Agent, or Firm—Rohm & Monsanto

[57] ABSTRACT

Functional electrical stimulation of regions of the skin of disabled individuals is achieved by delivering an energizing electrical signal via an electrode located in the region where the development of pressure sores is desired to be inhibited. Such electrical stimulation produces pressure variations as a result of tissue undulation at the interface where the skin of the human being meets a surface, such as the seat of a wheelchair. Additionally, blood flow is increased, muscles operate as blood pumps, and tissue bulk is increased. Electrical stimulation can be used to improve the conditioning of muscles of individuals who have been disabled for a long period of time, and the muscles have consequently atrophied, so that the beneficial effects of electrical stimulation to prevent or reduce the possibility of pressure sores is achieved.

11 Claims, No Drawings

FUNCTIONAL ELECTRICAL STIMULATION FOR PRESSURE SORE INHIBITION

BACKGROUND OF THE INVENTION

This invention relates generally to systems and arrangements for inhibiting the development of pressure sores, and more particularly to methods and arrangements for stimulating electrically in the region of a pressure communication where development of pressure sores can reasonably be expected.

It is well known that many physically disabled persons experience skin ulcerations, or pressure sores, when the skin is subjected to external pressure. The probability of developing pressure sores increases with the time over which the external pressure is applied, particularly if the pressure is applied without relief. The pressure sores which result from such relentless pressure are known by a variety of names, including "decubitus ulcers," "pressure sores," "ischemic sores," "bed sores," etc. Such sores, which will generally be referred to herein as "pressure sores," are a particular problem for individuals who are dependent upon wheelchairs. Many such individuals lack sensation in the buttocks.

Pressure sores are formed as a consequence of a number of intrinsic and extrinsic factors, including the magnitude of applied tissue force, force direction (i.e., normal versus shear), duration of applied force, friction, tissue hygiene, circulatory health, nutritional health, and other factors promoting tissue ischemia. The degree and duration of applied tissue pressure is recognized as an important factor in the formation of pressure sores. Any continued pressure sufficient to obstruct blood circulation for more than a few hours will lead to tissue necrosis and the probable formation of an ulcer or pressure sore.

It is known that increased tissue pressure creates ischemia resulting in the development of ulcers in muscle, skin, and other connective tissue. The microscopic changes in animal muscle resulting from the application of pressure were found to consist of edema, loss of cross-striations and myofibrials, hyalinization of fibers, neutrophilic infiltration, and phagocytosis by neutrophilis and macrophages. Changes in tissue produced after the application of localized pressure have been demonstrated to be primarily the result of ischemia. Intense pressure can cause complete cessation of capillary circulation and also results in the formation of venous thrombosis. The presence of venous thrombi then interferes with the normal reactive hyperemic vasodilation after the pressure is removed, resulting in continued ischemia.

The primary cause of tissue death with ischemia is due to reduced oxygen delivery and metabolite removal. Mean capillary pressure does not appear to be the primary parameter in the development of ischemia at the capillary level. Tissue ischemia can result from both supra and sub-normal capillary pressure, depending upon the direction of the applied force. Duration of the applied force, as well as force magnitude, is a critical factor in the formation of pressure sores. Researchers have found an inverse time-pressure relationship for the formation of pressure sores in laboratory animals. When the applied pressure is high enough to interfere with tissue circulation and is applied for a sufficient length of time, skin breakdown results. Duration of external pressure can be a more important factor in producing tissue damage than pressure magnitude.

Distortion and the eventual occlusion of blood vessels are primary results of uniaxial forces. The body tissue is essentially incompressible, so that during simple uniaxial compression, lateral expansion must occur to the extent required to maintain constant volume. This tissue distortion tends to collapse blood vessels and promote ulcer formation. Hydrostatic loading, on the other hand, avoids tissue distortion, a major factor in blood vessel occlusion. Thus, tissue distortion which occurs as a result of external forces, is a main factor in the development of pressure sores. Such external forces may be measured as increased pressure at the interface between the skin and a surface.

Shearing forces are also a significant factor in the formation of pressure sores. Non-homogeneity of skin results in increased stress and strain at the interfaces between the skin, underlying fat, fascia, muscle, and bone, with externally applied shear forces. This can be of special significance at the interface of the skin and subcutaneous tissues as many of the blood vessels which supply the skin enter this interface at right angles to its boundary. Forces in the plane of the skin produce deformation and bending in the vessels, therefore leading to ischemia. This can result in larger areas of ischemia when dealing with shear forces as compared to normal forces.

Other factors, in addition to the magnitude and duration of the normal and shear forces, have been found to play important roles in the formation of pressure sores. Friction, for example, increases the susceptibility of skin ulceration at constant pressure. Pressures of 45 mm Hg were found to cause ulcer formation when frictional forces were present. However, a pressure of 290 mm Hg was required to produce ulcers in swine with no friction present. Using isotope clearance techniques, it has been concluded that friction increases the production of ulcers by mechanical damage of the skin and not by an ischemic mechanism.

Several other secondary factors are invloved in the formation of pressure sores. Poor circulation conditions, edema, and anemia are all contributing factors in the formation of decubitus ulcers due to their restriction of oxygen delivery and metabolic processes. Moisture in the form of perspiration, urine, or feces, greatly contributes to the risk of ulcer formation. Pressure sores could be prevented by relieving body compression and washing the body daily to remove urine and feces. Keeping the skin clean and adequately ventilated is necessary to reduce bacterial growth and help prevent pressure sores.

Skin temperature is another important factor in the formation of pressure sores. Cold temperatures can facilitate development by promoting tissue ischemia via vasoconstriction. Hot temperatures, locally or in the form of fever, are also known to contribute to tissue breakdown. High temperatures contribute to cellular metabolic deficiency by increasing the metabolic rate, and hence, the tissue demand for blood and oxygen. This increased demand can be extremely detrimental when the blood supply is already compromised because of compression. High temperatures also increase the rate of sweat formation which has already been noted as a factor in the formation of pressure sores.

Two forms of pressure sores can be distinguished. The first is superficial and begins in the skin surface with maceration of devitalized skin. If permitted to progress, an infected shallow ulcer may be formed which is often painful for sensate individuals. The second type of pressure sore is the deep sore which arises in tissues overlying bony prominances and later extends to the surface. In this form, the progress of the tissue damage is from within to without and considerable necrosis of muscle, fascia, and subcutaneous tissue may have occurred even at a stage when the skin shows only erythema. Later, gangrenous lesions extend through the skin, and in some cases, down to underlying bone.

The financial costs for treating pressure sores are staggering. The average cost for hospitalized treatment of a pressure sore has been estimated at well over $15,000.00. Recently, cost of $20,000.00 to $30,000.00 per incident have been estimated. The annual price tag for medical care costs associated with pressure sores exceeds $2,000,000,000.00, and it is estimated that insurers allot 25% of anticipated spinal cord injury medical expenses for the treatment of pressure sores.

In addition to such financial costs, individuals afflicted with pressure sores also experience loss of work, reduced independence, inability to attend school, lowered self-esteem, particularly when forced to lay prone for periods of weeks or months, as well as other psychological burdens which are bourne by those afflicted and their families. Clearly, the problem is a devastating one, and there is a great need from both economic considerations and quality of life issues, for investigating new and more effective approaches to the problem. These problems, however, perhaps pale in the light of the fatality rate associated with pressure sores. The Veterans' Administration has estimated that 50% of all quadraplegic veterans and 30% of paraplegics will require hospitalization during their lifetime for pressure sore related problems. The Veterans' Administration also estimated that approximately 25% of these patients would die as a direct consequence of pressure sores.

In response to this urgent need, there is available in the prior art a large variety of mattresses, special beds, wheelchair cushions and other support systems. Most such systems are designed to reduce pressures or distribute them more evenly over the body. Although some of these devices have succeeded commercially, none seems to provide a universal solution to the problem of ulcer formation.

It is, therefore, an object of this invention to provide a simple and relatively inexpensive system for inhibiting the development of pressure sores.

It is also an object of this invention to provide a system which reduces the risks of pressure sores without restricting wheelchair mobility.

It is another object of this invention to provide a system for inhibiting the development of pressure sores, which can be used by sensate and insensate individuals.

SUMMARY OF THE INVENTION

The foregoing and other objects are achieved by this invention which provides a system for inhibiting development of pressure sores in the skin of a living being. An electrode is applied to the skin of the living being in the general vicinity of the region of the skin where development of the pressure sore is to be inhibited. Such application of the electrode establishes electrical communication between the electrode and the skin of the living being. An energizing electrical signal is delivered to the skin of the living being via the electrode such that a skin displacement is achieved in the region of the skin where the pressure sores are to be inhibited. Such skin displacement is responsive to the energizing electrical signal.

Ordinarily, the region of skin where the displacement is desired to be achieved is to be subjected to an external pressure. The displacement of the skin, which may be periodic or undulating, is intended to enhance the supply of oxygen to the affected skin and the removal of metabolites. A number of mechanisms may be at work in prevention of pressure sores. These include interface pressure variation resulting in tissue undulation, increased blood flow, muscle pump activity, and increased tissue bulk. Such positive aspects, however, must be weighed against the negative aspects of such electrical stimulation such as increased intramusculature pressure, increased muscle oxygen requirements, increased metabolite production, increased fatigue, increased heat, and increased perspiration.

In accordance with an apparatus aspect of the invention, an arrangement for inhibiting development of pressure sores in the skin of a human being employs a signal generator for producing a stimulating electrical signal. A first electrode couples the signal generator to the skin of the human being so that the stimulating electrical signal is conducted to the skin of the human being to produce a responsive displacement of the skin in the vicinity of a pressure communication. In one embodiment, the second electrode is arranged on the skin of the human being at a predetermined location with respect to the first electrode. The location of the second electrode may be determined to be a point of maximum displacement of the skin in response to a prior electrical stimulation. The prior electrical stimulation may be monopolar, and the point of maximum displacement of the skin is identified by visual inspection during such monopolar stimulation.

Generally, such displacement is achieved by conducting the stimulating electrical signal through the skin of the human being through the underlying muscle in the vicinity of the pressure communication. In situations where the anatomical region of the human being where pressure sore development is desired to be inhibited is in the vicinity of the buttocks, or gluteus maximus, such as for a wheelchair dependent individual, the electrodes are connected in the vicinity of the gluteus maximus. More specifically, one electrode, illustratively the anode, is placed on the sacrum and the other electrode, the cathode, is placed at a point which is located approximately one-third of the distance from the sacrum to the greater trochanter, superior to the sitting surface.

DETAILED DESCRIPTION OF EXPERIMENTS AND RESULTS

Experiment 1—Pressure Measurements

Methods

Bilateral stimulation of the gluteus maximus was performed on a subject while seated in a wheelchair. Seating interface pressure changes were monitored as a measure of tissue undulation.

Stimulation of the gluteus maximus was provided by a dual channel neuromuscular stimulator (Respond II by Medtronics, Inc.). Controllable features of the stimulator include signal amplitude, pulse rate, and signal "on" and "off" times. A Scimedics Pressure Evaluator Pad was used to monitor interface pressure changes. This pad operates by closing an electrical contact and turning on an indicator light whenever the interface pressure exceeds pad pressure.

Two able-bodied subjects were treated. Prior to measurements, surface stimulating electrodes were placed bilaterally upon the gluteus maximus with the subject in a prone position. Cathodes were positioned at the point of maximum contraction for a given stimulus intensity as determined through monopolar stimulation and visual inspection of the response. In general, this point was located approximately one-third of the distance from the sacrum to the greater trochanter, superior to the sitting surface. The anode was placed on the sacrum.

Once the electrodes were in place, the Scimedics Pressure Evaluator Pad was secured beneath the ischial tuberosity. The subject was then seated in a wheelchair with:

(1) backrest to seat angle of at least 80 degree;
(2) a minimum 2 inch clearance from the popliteal fossa to the forward edge of the wheelchair; and
(3) foot rest adjusted to keep the thighs parallel to the seat and floor.

Stimulation intensity was set at a level eliciting approximately a one-inch medial-lateral movement of the knee with the subject seated and the pulse rate at 3 per second. This level of stimulation has been easily tolerated by all sensate subjects.

A series of trials were conducted to determine maximum pressure variations produced with functional electrical stimulation. In each trial, the Scimedics pad was inflated to the interface pressure (i.e., until the indicator light had just turned off). Pad pressure was then lowered incrementally until stimulation did not produce a measurable change of interface pressure (by turning the indicator light off). The difference between the initial pad pressure and the final pad pressure was recorded as the maximum interface pressure change induced with functional electrical stimulation.

Trials for each set of stimulation parameters shown in Table I were performed. Each trial consisted of approximately 15 seconds of stimulation. There was at least 2 minutes of rest between each trial with pressure relief of the sitting surface allowed. The entire set of trials was repeated two additional times to test reproducibility. This protocol was used with all four seating surfaces listed in Table II.

TABLE I

| STIMULATION PARAMETERS | | |
|---|---|---|
| Rate (per sec) | Cycle On (sec) | Cycle Off (sec) |
| 3 | 15 | — |
| 5 | 15 | — |
| 10 | 5 | 2 |
| 30 | 5 | 10 |
| 50 | 2 | 10 |

Results

A summary of the maximum interface pressure changes induced through functional electrical stimulation is listed below in Table II. All maximum values are in mm of Hg and were produced using a pulse rate of 50/second for 2 seconds.

TABLE II

| MAXIMUM PRESSURE VARIATIONS WITH FUNCTIONAL ELECTRICAL STIMULATION | | |
|---|---|---|
| Surface | Subject A (mean + sd) | Subject B (mean + sd) |
| slung seat | 9.44 + 1.42 | 10.11 + 1.69 |
| 1" gel pad | 5.00 + 1.10 | 15.83 + 4.90 |
| temper foam | 2.67 + 1.15 | 10.67 + 2.31 |
| high profile ROHO | 4.17 + 0.98 | 11.67 + 6.22 |

Experiment 2—Fatigue Study

Methods

Interface pressure changes from functional electrical stimulation were observed to deteriorate with extended periods of stimulation. This fatigue effect was studied in the following manner:

Two able bodied subjects were studied while seated in a standard wheelchair with a slung seat. Stimulation electrodes were applied, and intensities were set as previously described in Experiment 1. The gluteus maximus was stimulated at 50 pulses/second with an "on" time of 2 seconds and an "off" time of 5 seconds. This level of stimulation induced an interface pressure change between 5 and 15 mm Hg in both subjects.

Stimulation was continued until a predetermined pressure change could no longer be produced for three consecutive stimulations. A 5 mm criteria was used for subject A and a 10 mm criteria was used for subject B (due to his fatigue resistance). The number of stimulations needed to reach this fatigue point was recorded. This protocol was repeated twice, each after five minutes rest and once or twice again after an additional 15 minute rest.

Results

The results are shown below in Table III. A fatigue effect was obvious in both subjects. Subject B was considerably more fatigue resistant than subject A. This experiment was repeated with subject B on a different day with similar results.

TABLE III

| FATIGUE STUDY RESULTS | | |
|---|---|---|
| | STIMULATIONS TO FATIGUE | |
| TRIAL | Subject A | Subject B |
| 1. Initial Stimulation | 15 | 57 |
| 2. After 5 Minute Rest | 2 | 29 |
| 3. After 5 Minute Rest | 5 | 17 |
| 4. After 5 Minute Rest | — | 6 |
| 5. After 30 Minute Rest | 12 | 42 |
| 6. After 5 Minute Rest | 3 | 35 |
| 7. After 5 Minute Rest | — | 21 |

It has been learned that functional electrical stimulation can make appreciable changes in the buttock configuration of a seated able-bodied person. The pressure experiment discussed hereinabove produced pressure measurements with substantial inherent error, but also provided a somewhat quantitative indication of changes in the configuration of the tissue. It is to be noted, however, that the results obtained with able-bodied individuals may not be obtainable from a paralyzed individual, particularly one who has had no active contractions of the buttocks for many years with associated muscular atrophy. In such a case, electrical stimulation can be used to improve muscle function to the point where substantially the same effects can be produced.

Although the invention has been described in terms of specific embodiments and applications, persons skilled in the art can, in light of this teaching, generate additional embodiments without exceeding the scope or departing from the spirit of the claimed invention. Accordingly, it is to be understood that the descriptions herein are proffered to facilitate comprehension of the invention and should not be construed to limit the scope thereof.

What is claimed is:

1. A method of inhibiting development of pressure sores in the tissue of a living being, the method comprising the steps of:

first applying to an area of skin of the living being an electrode in the vicinity of a region of the tissue where development of the pressure sore is to be inhibited, whereby electrical communication is established between said electrode and the tissue of the living being;

second applying to the skin of the living being in the vicinity of said region of the tissue where the development of a pressure sore is to be inhibited an external force whereby the tissue in said region is distorted and blood flow therethrough is diminished; and delivering an energizing electrical signal to the skin of the living being via said electrode whereby an undulation of the tissue is achieved in said region, said undulation of the tissue being operative to relieve at least intermittently said external force in response to said energizing signal.

2. The method of claim 1 wherein the living being is a human being and said step of second applying said region of the tissue to a force includes the step of sitting of said human being whereby said region of the tissue is in the vicinity of the gluteus maximus of the human being.

3. The method of claim 1 wherein said step of first applying comprises the further step of selecting an electrode location.

4. The method of claim 3 wherein said step of selecting comprises the further steps of:

stimulating electrically said vicinity of said region of the tissue where development of the pressure sores is to be inhibited;

inspecting visually said vicinity of said region of the tissue; and identifying a subregion in said vicinity of said region of the tissue in response to said steps of stimulating and inspecting, where said electrode is to be applied.

5. The method of claim 4 wherein said step of identifying said subregion is performed in response to an undulation of the tissue in response to said step of stimulating.

6. The method of claim 5 wherein said subregion where said electrode is to be applied corresponds to a point of maximum amplitude of undulation displacement of the tissue in response to a monopolar excitation.

7. The method of claim 4 wherein said living being is a human being and said subregion is located approximately one-third of the distance from the sacrum to the greater prochanter, superior to the sitting surface, and there is further provided the step of applying to the tissue of the living being a further electrode in the vicinity of said sacrum.

8. The method of claim 1 wherein prior to performing said step of first applying there is provided the further step of strengthening a muscle underlying said vicinity of said region of the tissue.

9. The method of claim 8 wherein said step of strengthening comprises the further step of conditioning said muscle by electrical stimulation whereby a resistance to fatigue of said muscle is improved.

10. The method of claim 9 wherein said step of conditioning comprises the further step of increasing the vascular density of said muscle.

11. A method of inhibiting development of pressure sores in the tissue of a human being who is in pressure communication with a surface, the method comprising the steps of:

applying a monopolar electrical signal to the human being;

identifying a location on skin of the human being of maximum tissue displacement responsive to said monopolar electrical signal;

producing by a signal generator a stimulating electrical signal;

coupling said signal generator electrically by a first electrode to a first predetermined location on the skin of the human being; and coupling said signal generator means to a second predetermined location on the skin of the human being by a second electrode, said second predetermined location being said identified location of maximum displacement of the tissue of the human being in response to said monopolar signal.

* * * * *